(12) United States Patent
Yamagawa et al.

(10) Patent No.: US 10,653,586 B2
(45) Date of Patent: May 19, 2020

(54) CURABLE COMPOSITION, CURABLE COMPOSITION FOR DENTAL USE, AND ORGANIC-INORGANIC COMPOSITE PARTICLES FOR DENTAL USE

(71) Applicant: TOKUYAMA DENTAL CORPORATION, Tokyo (JP)

(72) Inventors: Junichiro Yamagawa, Tokyo (JP); Tatsuya Yamazaki, Tokyo (JP); Takuma Matsuo, Tokyo (JP); Takuya Suzuki, Tokyo (JP)

(73) Assignee: TOKUYAMA DENTAL COOPERATION (JP)

( * ) Notice: Subject to any disclaimer, the term of this patent is extended or adjusted under 35 U.S.C. 154(b) by 0 days.

(21) Appl. No.: 15/760,535

(22) PCT Filed: Oct. 27, 2016

(86) PCT No.: PCT/JP2016/081878
§ 371 (c)(1),
(2) Date: Mar. 15, 2018

(87) PCT Pub. No.: WO2017/073664
PCT Pub. Date: May 4, 2017

(65) Prior Publication Data
US 2019/0038515 A1     Feb. 7, 2019

(30) Foreign Application Priority Data

Oct. 28, 2015   (JP) ................. 2015-211882

(51) Int. Cl.
| | | |
|---|---|---|
| A61K 6/08 | (2006.01) | |
| A61K 6/76 | (2020.01) | |
| C09C 1/28 | (2006.01) | |
| C09C 3/10 | (2006.01) | |
| A61K 6/62 | (2020.01) | |
| A61K 6/884 | (2020.01) | |
| A61K 6/887 | (2020.01) | |

(52) U.S. Cl.
CPC ............. *A61K 6/76* (2020.01); *A61K 6/62* (2020.01); *A61K 6/884* (2020.01); *A61K 6/887* (2020.01); *C09C 1/28* (2013.01); *C09C 3/10* (2013.01); *C01P 2004/32* (2013.01); *C01P 2004/62* (2013.01)

(58) Field of Classification Search
CPC .................................................. A61K 6/0002
See application file for complete search history.

(56) References Cited

U.S. PATENT DOCUMENTS

| | | | | |
|---|---|---|---|---|
| 5,990,195 A | * | 11/1999 | Arita | ..... A61K 6/083 523/115 |
| 2013/0005846 A1 | * | 1/2013 | Yamazaki | ........... A61K 6/0073 521/149 |
| 2013/0324635 A1 | * | 12/2013 | Shimizu | ............... A61K 6/0017 522/173 |
| 2014/0206792 A1 | * | 7/2014 | Ishizaka | ............... A61K 6/0005 523/115 |
| 2014/0213687 A1 | | 7/2014 | Yamazaki et al. | |
| 2015/0011673 A1 | | 1/2015 | Yamagawa et al. | |

FOREIGN PATENT DOCUMENTS

| | | |
|---|---|---|
| JP | 2000-080013 A | 3/2000 |
| JP | 2013-144778 A | 7/2013 |
| JP | 2014-177443 A | 9/2014 |
| JP | 2015-105254 A | 6/2015 |
| WO | WO-2013-039169 A1 | 3/2013 |

* cited by examiner

*Primary Examiner* — Michael F Pepitone
(74) *Attorney, Agent, or Firm* — Harness, Dickey & Pierce, P.L.C.

(57) ABSTRACT

To provide a cured product having high fracture energy, provided are a curable composition, including: organic-inorganic composite particles; (a polymerizable monomer; a polymerization initiator; and inorganic particles, in which a cured body formed by curing the curable composition includes: a matrix formed by curing all constituent components of the curable composition except for the organic-inorganic composite particles; and the organic-inorganic composite particles dispersed and contained in the cured body, and in which an elastic modulus M of the matrix is larger than an elastic modulus P of the organic-inorganic composite particles by 3.0 GPa or more, a curable composition for dental use, and an organic-inorganic composite particle for dental use.

4 Claims, No Drawings

CURABLE COMPOSITION, CURABLE COMPOSITION FOR DENTAL USE, AND ORGANIC-INORGANIC COMPOSITE PARTICLES FOR DENTAL USE

CROSS-REFERENCE TO RELATED APPLICATIONS

This application is a U.S. National Stage application of International Application No. PCT/JP2016/081878, filed on Oct. 27, 2016, which claims priority to Japanese Patent Application No. 2015-211882, filed on Oct. 28, 2015. The entire disclosures of the above applications are expressly incorporated by reference herein.

BACKGROUND

Technical Field

The present invention relates to a curable composition, a curable composition for dental use, and an organic-inorganic composite particle for dental use.

Related Art

A curable composition formed of a polymerizable monomer and a filler is used in various fields from the viewpoints of mechanical strength and simplicity of work.

In the curable composition, selection of the filler is important, and the curable composition is formed by selecting, for example, the material, shape, particle diameter, and filling amount of the filler to be used. Through appropriate selection thereof, various properties, such as mechanical strength, physical characteristics, optical characteristics, and workability, of a final product are optimally adjusted.

For example, a curable composition for dental use generally includes a polymerizable monomer, a filler, and a polymerization initiator as main components, and is applied as a composite resin, a hard resin, an artificial tooth, cement, a resin material for machining processing, or the like. The curable composition for dental use is widely used as a dental material because of its ease of handling and low harmfulness to a living body. However, as compared to other materials, such as a metal and a ceramic, the curable composition for dental use can be hardly said to be sufficient yet in terms of mechanical strength required in order to function in a severe oral environment, and still needs to be improved also from the viewpoint of simultaneously achieving the mechanical strength and other physical properties, such as aesthetics and workability.

Under such situation, organic-inorganic composite particles are often used as the filler. For example, according to JP 2000-80013, when the organic-inorganic composite particles are used, a curable composition for dental use having a paste form and having excellent workability can be obtained while excellent surface smoothness and wear resistance are maintained, and moreover, its polymerization shrinkage rate is small. The organic-inorganic composite particles are composite particles each containing fine inorganic particles in an organic resin. The organic-inorganic composite particles have a smaller specific surface area than that of the fine inorganic particles. Therefore, the curable composition for dental use having a paste form can be produced by blending a sufficient amount of the organic-inorganic composite particles without expressing a thickening action. The curable composition for dental use produced by this method has had the following problem: in a cured body obtained by curing the composition, bonding at an interface between each of the organic-inorganic composite particles and its surrounding matrix is weak, and hence strength of the cured body is low.

In WO 2013/039169, there is a proposal of using organic-inorganic composite particles having aggregation gaps and having a micropore volume measured by a mercury intrusion method (in this case, the micropore refers to a pore having a micropore diameter in the range of from 1 nm to 500 nm) of from 0.01 $cm^3/g$ to 0.30 $cm^3/g$. According to WO 2013/039169, when the organic-inorganic composite particles having aggregation gaps are used, a polymerizable monomer of a curable composition penetrates the organic-inorganic composite particles due to capillarity and is then cured, and hence an anchoring effect occurs to retain the organic-inorganic composite particles in a cured body of the curable composition with high interlocking strength, resulting in an improvement in mechanical strength.

In addition, in JP 2015-105254 A, it is described that, in a curable composition for dental use having blended therein organic-inorganic composite particles having aggregation gaps, when an organic resin component of each of the organic-inorganic composite particles is one obtained by polymerizing a polymerizable monomer component containing a certain amount or more of a polymerizable monomer having a hydrogen-bonding functional group, and a certain amount or more of a polymerizable monomer having a hydrogen-bonding functional group is blended as a polymerizable monomer component constituting an organic matrix, there is obtained a curable composition for dental use capable of providing a cured body having even higher mechanical strength.

As a typical method of evaluating the mechanical strength of a final product, there is given bending strength that is a stress value calculated on the basis of the maximum load applied to the product in a bending test. In the case of an organic-inorganic composite material obtained by curing a curable composition formed of a polymerizable monomer and an inorganic filler, in general, as the content of the inorganic filler is increased, the maximum load tends to increase, i.e., the bending strength tends to increase. However, as the amount of the inorganic filler increases, brittleness resulting from a decrease in amount of a resin serving as a binder also tends to increase. Therefore, it is considered that the bending strength and resistance to fracture do not necessarily coincide with each other. Meanwhile, total energy applied to a material until its fracture is called fracture energy. The fracture energy is a numerical value obtained on the basis of an integrated value up to fracture in a stress-strain curve, and may be rather important in evaluating the mechanical strength of an organic-inorganic composite material in which some degree of strain is generated.

The present invention has been made in view of the above-mentioned circumstances, and an object of the present invention is to provide a curable composition capable of providing a cured product having high fracture energy, a curable composition for dental use using the curable composition, and an organic-inorganic composite particle for dental use to be used for the curable composition for dental use.

SUMMARY

The inventors of the present invention have made extensive investigations in order to achieve the above-mentioned object. As a result, the inventors of the present invention have found that, in a curable composition having blended therein organic-inorganic composite particles, it is effective to set the elastic modulus of the organic-inorganic composite particles to be relatively low with respect to that of a matrix formed by curing components except for the organic-inorganic composite particles. The inventors have also found that, as a result of the foregoing, phases having a relatively low elastic modulus (i.e., the organic-inorganic composite particles) can be locally formed in a cured body obtained by curing the curable composition, and hence a curable composition capable of providing a cured body having high fracture energy is obtained. Thus, the inventors have completed the present invention.

That is, according to one embodiment of the present invention, there is provided a curable composition, including: (A) organic-inorganic composite particles; (B) a polymerizable monomer; (C) a polymerization initiator; and (D) inorganic particles, in which a cured body formed by curing the curable composition includes: a matrix formed by curing all constituent components of the curable composition except for (A) the organic-inorganic composite particles; and (A) the organic-inorganic composite particles dispersed and contained in the cured body, and in which an elastic modulus M of the matrix is larger than an elastic modulus P of (A) the organic-inorganic composite particles by 3.0 GPa or more.

In the curable composition according to one embodiment of the present invention, it is preferred that the elastic modulus P of (A) the organic-inorganic composite particles be from 0.01 GPa to 12.0 GPa, and the elastic modulus M of the matrix be from 6.0 GPa to 30.0 GPa.

In the curable composition according to another embodiment of the present invention, it is preferred that (A) the organic-inorganic composite particles have micropores, and (A) the organic-inorganic composite particles that have micropores have a micropore volume of from 0.01 cm$^3$/g to 0.30 cm$^3$/g.

In the curable composition according to another embodiment of the present invention, it is preferred that (A-1) an organic resin for forming each of (A) the organic-inorganic composite particles include a cured body of (a-1) a polymerizable monomer having a molecular weight per polymerizable functional group contained in a molecule of from 230 to 1,000.

In the curable composition according to another embodiment of the present invention, it is preferred that (A-1) an organic resin for forming each of (A) the organic-inorganic composite particles include a cured body of (a-1) a polymerizable monomer having a molecular weight per polymerizable functional group contained in a molecule of from 230 to 1,000, and a molecular weight per polymerizable functional group contained in (B) the polymerizable monomer be from 35 to 250.

It is preferred that the curable composition according to another embodiment of the present invention include a curable composition for dental use.

According to one embodiment of the present invention, there is provided a curable composition for dental use, including the curable composition of the present invention.

According to one embodiment of the present invention, there is provided an organic-inorganic composite particle for dental use, which is used for a curable composition for dental use including (A) organic-inorganic composite particles having an elastic modulus P of from 0.01 GPa to 12.0 GPa, (B) a polymerizable monomer, (C) a polymerization initiator, and (D) inorganic particles, in which a cured body formed by curing the curable composition for dental use includes: a matrix formed by curing all constituent components of the curable composition for dental use except for (A) the organic-inorganic composite particles; and (A) the organic-inorganic composite particles dispersed and contained in the cured body, and in which the matrix has an elastic modulus M of from 6.0 GPa to 30.0 GPa.

ADVANTAGEOUS EFFECTS OF INVENTION

According to the present invention, the curable composition capable of providing a cured product having high fracture energy, the curable composition for dental use using the curable composition, and the organic-inorganic composite particle for dental use to be used for the curable composition for dental use can be provided.

DETAILED DESCRIPTION

A curable composition according to one embodiment of the present invention includes: (A) organic-inorganic composite particles; (B) a polymerizable monomer; (C) a polymerization initiator; and (D) inorganic particles, in which a cured body formed by curing the curable composition includes: a matrix formed by curing all constituent components of the curable composition except for (A) the organic-inorganic composite particles; and (A) the organic-inorganic composite particles dispersed and contained in the cured body, and in which an elastic modulus M of the matrix is larger than an elastic modulus P of (A) the organic-inorganic composite particles by 3.0 GPa or more as shown in the following expression (1).

$$\text{Elastic modulus } M\text{-elastic modulus } P \geq 3.0 \text{ GPa} \qquad \text{Expression (1)}$$

Herein, all constituent components of the curable composition except for (A) the organic-inorganic composite particles only need to include at least (B) the polymerizable monomer, (C) the polymerization initiator, and (D) the inorganic particles, and may, for example, <i> further include a component other than the components (A) to (D) in addition to the components (B) to (D), or <ii> include only the components (B) to (D). In the case <i> where a component other than the components (A) to (D) is further included in addition to the components (B) to (D), the blending amount of the other component in the curable composition is not particularly limited, but is preferably 20 mass % or less, preferably 10 mass % or less, still more preferably 5 mass % or less. In addition, the matrix contains a resin component formed by curing at least (B) the polymerizable monomer as a main component, and (D) the inorganic particles dispersed in the resin component.

The elastic modulus P of (A) the organic-inorganic composite particles and the elastic modulus M of the matrix are measured as described below. That is, required components are weighed and kneaded to produce the curable composition according to this embodiment containing the components (A) to (D). Then, the curable composition is polymerized and cured to produce a cured body. Next, a cut surface of the cured body is polished with a microtome. An elastic modulus obtained by measuring, with a micro hardness tester, an elastic modulus in a measurement area formed only of a portion in the polished cut surface in which (A) the organic-inorganic composite particles are present is defined as the elastic modulus P of (A) the organic-inorganic composite particles. In addition, an elastic modulus obtained by measuring, with a micro hardness tester, an elastic modulus in a measurement area formed of a portion in the polished cut surface of the cured body other than the portion in which (A) the organic-inorganic composite particles are present is defined as the elastic modulus M of the matrix. The elastic moduli P and M are values corresponding to Young's moduli measured in conformity to ISO 14577, and are measured using a nanoindentation hardness tester. The measurement is performed under an environment having a temperature of 23° C. and a relative humidity of 50%. With regard to an indenter shape, a Berkovich indenter ($\alpha=65°$) is used. As a Poisson's ratio, the Poisson's ratio of a cured body obtained by curing the curable composition is used. A test load, a loading speed, an unloading speed, and a maximum load duration are as follows: test load: 2.5 mN; loading speed: 0.5 mN/sec; unloading speed: 0.5 mN/sec; and maximum load duration: 1 second.

(A) Organic-inorganic Composite Particles

The curable composition according to this embodiment contains (A) the organic-inorganic composite particles. The organic-inorganic composite particles are each a particle which contains (A-1) an organic resin and (A-2) inorganic particles, which has a structure in which (A-2) the inorganic particles are dispersed in (A-1) the organic resin, and in which (A-1) the organic resin and (A-2) the inorganic particles are composited with each other.

Kind of (A-1) Organic Resin

As (A-1) the organic resin for forming each of (A) the organic-inorganic composite particles to be used for the curable composition according to this embodiment, any known organic resin capable of satisfying the expression (1) may be used without any limitation. Any of a thermoplastic resin and a thermosetting resin may be used, and a resin having high transparency is preferred from the viewpoint of a design property. Specifically, an acrylic resin such as polymethyl methacrylate, polystyrene, polyamide, polycarbonate, a polyester resin such as polyethylene terephthalate, a methyl methacrylate-butadiene-styrene resin, an acrylonitrile-butadiene-styrene resin, a cycloolefin resin, an epoxy resin, or an oxetane resin, or a copolymer thereof may be suitably used. Of those, an acrylic resin, an epoxy resin, or an oxetane resin is particularly suitably used because of its safety, high transparency, and ease of refractive index control.

(A-1) The organic resin preferably shows fluidity in a process of being mixed with (A-2) the inorganic particles in order to easily disperse (A-2) the inorganic particles in (A-1) the organic resin. (A) The organic-inorganic composite particles may be produced by mixing and dispersing (A-2) the inorganic particles in (A-1) the organic resin in a molten state, or (A) the organic-inorganic composite particles may be produced by dispersing in advance (A-2) the inorganic particles in (a-1) a polymerizable monomer to be used for the production of (A-1) the organic resin, polymerizing and curing (a-1) the polymerizable monomer, and as required, performing treatment for turning the resultant into fine particles. However, in order that (A) the organic-inorganic composite particles to be used for the curable composition according to this embodiment may be easily produced, (A) the organic-inorganic composite particles are preferably particles obtained by polymerizing and curing (a-1) the polymerizable monomer having dispersed and incorporated therein (A-2) the inorganic particles. In this case, (a-1) the polymerizable monomer is preferably a polymerizable monomer having compatibility with an organic solvent, such as acetone or ethanol.

(a-1) The polymerizable monomer is not particularly limited, and examples thereof include a radically polymerizable monomer and a cationically polymerizable monomer, such as an epoxy compound or an oxetane compound. A (meth)acrylate-based polymerizable monomer, such as an acrylate or a methacrylate, is suitably used as the radically polymerizable monomer because of its good polymerizability and the like. Specific examples of the (meth)acrylate-based polymerizable monomer include the following.

(a-1) Kind of Polymerizable Monomer (a-1-1) Monofunctional Radically Polymerizable Monomer Examples thereof may include: methyl (meth)acrylate, ethyl (meth)acrylate, n-butyl (meth)acrylate, 2-ethylhexyl (meth)acrylate, n-lauryl (meth)acrylate, n-stearyl (meth)acrylate, tetrafurfuryl (meth)acrylate, glycidyl (meth)acrylate, methoxyethylene glycol (meth)acrylate, methoxydiethylene glycol (meth)acrylate, methoxytriethylene glycol (meth)acrylate, methoxypolyethylene glycol (meth)acrylate, ethoxyethylene glycol (meth)acrylate, ethoxydiethylene glycol (meth)acrylate, ethoxytriethylene glycol (meth)acrylate, ethoxypolyethylene glycol (meth)acrylate, phenoxyethylene glycol (meth)acrylate, phenoxydiethylene glycol (meth)acrylate, phenoxytriethylene glycol (meth)acrylate, phenoxypolyethylene glycol (meth)acrylate, cyclohexyl (meth)acrylate, benzyl (meth)acrylate, isobornyl (meth)acrylate, and trifluoroethyl (meth)acrylate; monofunctional polymerizable monomers each having an acidic group, such as (meth)acrylic acid, N-(meth)acryloylglycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen maleate, 6-(meth)acryloyloxyethylnaphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth) acryloyloxybenzoic acid, 3-(meth) acryloyloxybenzoic acid, 4-(meth)acryloyloxybenzoic acid, N-(meth)acryloyl-5-aminosalicylic acid, and N-(meth)acryloyl-4-aminosalicylic acid, and compounds obtained by converting carboxyl groups of those compounds into acid anhydride groups, 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propyl succinate, 4-(2-(meth)acryloyloxyethyl)trimellitate anhydride, 4-(2-(meth)acryloyloxyethyl)trimellitate, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 4-(meth)acryloyloxybutyl trimellitate, 6-(meth)acryloyloxyethylnaphthalene-1,2,6-tricarboxylic anhydride, 6-(meth)acryloyloxyethylnaphthalene-2,3,6-tricarboxylic anhydride, 4-(meth)acryloyloxyethylcarbonylpropionoyl-1,8-naphthalic anhydride, 4-(meth)acryloyloxyethylnaphthalene-1,8-tricarboxylic anhydride, 9-(meth)acryloyloxynonane-1,1-dicarboxylic acid, 13-(meth)acryloyloxytridecane-1,1-dicarboxylic acid, 11-(meth)acrylamidoundecane-1,1-dicarboxylic acid, 2-(meth)acryloyloxyethyl dihydrogen phosphate, 2-(meth)acryloyloxyethylphenyl hydrogen phosphate, 10-(meth)acryloyloxydecyl dihydrogen phosphate, 6-(meth)acryloyloxyhexyl dihydrogen phosphate, 2-(meth)acryloyloxyethyl-2-bromoethyl hydrogen phosphate, 2-(meth)acrylamidoethyl dihydrogen phosphate, 2-(meth)acrylamido-2-methylpropanesulfonic acid, 10-sulfodecyl (meth)acrylate, 3-(meth)acryloxypropyl-3-phosphonopropionate, 3-(meth)acryloxypropyl phosphonoacetate, 4-(meth)acryloxybutyl-3-phosphonopropionate, 4-(meth)acryloxybutyl phosphonoacetate, 5-(meth)acryloxypentyl-3-phosphonopropionate, 5-(meth)acryloxypentyl phosphonoacetate, 6-(meth)acryloxyhexyl-3-phosphonopropionate, 6-(meth)acryloxyhexyl phosphonoacetate, 10-(meth)acryloxydecyl-3-phosphonopropionate, 10-(meth)acryloxydecyl phosphonoacetate, 2-(meth)acryloxyethylphenylphosphonate, 2-(meth)acryloyloxyethylphosphonic acid, 10-(meth)acryloyloxydecylphosphonic acid, N-(meth)acryloyl-ω-aminopropylphosphonic acid, 2-(meth)acryloyloxyethylphenyl hydrogen phosphate, 2-(meth)acryloyloxyethyl-2'-bromoethyl hydrogen phosphate, and 2-(meth)acryloyloxyethylphenyl phosphonate; and monofunctional polymerizable monomers each having a hydroxy group, such as 2-hydroxyethyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, and N,N-(dihydroxyethyl) (meth)acrylamide.

(a-1-2) Bifunctional Radically Polymerizable Monomer

Examples thereof may include: 2,2-bis(methacryloyloxyphenyl)propane, 2,2-bis(4-methacryloyloxyethoxyphenyl)propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxydiethoxyphenyl)propane, 2(4-methacryloyloxydiethoxyphenyl)-2(4-methacryloyloxytriethoxylphenyl)propane, 2(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, and acrylates corresponding to those methacrylates; diadducts obtained by addition of vinyl monomers each having a —OH group, including methacrylates, such as 2-hydroxyethyl methacrylate, 2-hydroxypropyl methacrylate, and 3-chloro-2-hydroxypropyl methacrylate, or acrylates corresponding to those methacrylates, and diisocyanate compounds each having an aromatic group, such as diisocyanatomethylbenzene and 4,4'-diphenylmethane diisocyanate, and ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to those methacrylates; diadducts obtained by addition of vinyl monomers each having a —OH group, including methacrylates, such as 2-hydroxyethyl methacrylate, 2-hydroxypropyl methacrylate, and 3-chloro-2-hydroxypropyl methacrylate, or acrylates corresponding to those methacrylates, and diisocyanate compounds, such as hexamethylene diisocyanate, trimethylhexamethylene diisocyanate, diisocyanatomethylcyclohexane, isophorone diisocyanate, and methylenebis(4-cyclohexyl isocyanate), for example, 1,6-bis(methacrylethyloxycarbonylamino)-2,2-4-trimethylhexane; and compounds each containing an acidic group, such as acrylic anhydride, methacrylic anhydride, di(2-methacryloyloxypropyl)phosphate, di[2-(meth)acryloyloxyethyl] hydrogen phosphate, di[4-(meth)acryloyloxybutyl] hydrogen phosphate, di[6-(meth)acryloyloxyhexyl] hydrogen phosphate, di[8-(meth)acryloyloxyoctyl] hydrogen phosphate, di[9-(meth)acryloyloxynonyl] hydrogen phosphate, di[10-(meth)acryloyloxydecyl] hydrogen phosphate, and 1,3-di(meth)acryloyloxypropyl-2-dihydrogen phosphate.

(a-1-3) Trifunctional Radically Polymerizable Monomer

Examples thereof may include trimethylolpropane tri(meth)acrylate, trimethylolethane tri(meth)acrylate, pentaerythritol tri(meth)acrylate, dipentaerythritol tri(meth)acrylate, ethoxylated trimethylolpropane tri(meth)acrylate, propoxylated trimethylolpropane tri(meth)acrylate, and tris(2-(meth)acryloxyethyl isocyanurate).

(a-1-4) Tetrafunctional Radically Polymerizable Monomer

There may be suitably used, for example: tetra(meth)acrylate compounds, such as pentaerythritol tetra(meth)acrylate, ethoxylated pentaerythritol tetra(meth) acrylate, propoxylated pentaerythritol tetra(meth)acrylate, and ethoxylated ditrimethylolpropane tetra(meth)acrylate; and diisocyanate compounds each having an aliphatic group between two isocyanate groups, such as hexamethyl diisocyanate, trimethylhexamethylene diisocyanate, and diisocyanatomethylcyclohexane.

(a-1) The polymerizable monomer is preferably a polymerizable monomer that is bifunctional or higher functional, more suitably bifunctional to tetrafunctional, most suitably bifunctional for, for example, the following reasons: the polymerizability is high; and a cured body obtained using (a-1) the polymerizable monomer has particularly high mechanical physical properties.

In addition, the polymerizable monomers may be used alone or in combination thereof.

Polymerization Initiator

When (A-1) the organic resin for forming each of (A) the organic-inorganic composite particles is formed using (a-1) the polymerizable monomer, a polymerization initiator is preferably used in order to polymerize and cure the polymerizable monomer. General polymerization methods include: a polymerization method based on a reaction caused by light energy, such as ultraviolet light or visible light (hereinafter referred to as photopolymerization); a polymerization method based on a chemical reaction between a peroxide and a promoter; and a polymerization method based on thermal energy (hereinafter referred to as thermal polymerization). Any of the methods may be used for the polymerization of (a-1) the polymerizable monomer. Of those, photopolymerization or thermal polymerization is preferred because the timing of the polymerization can be arbitrarily selected on the basis of the energy to be externally applied, such as light or heat, and the operation is simple. Any of the following various polymerization initiators may be appropriately selected and used depending on the polymerization method to be adopted.

As a photopolymerization initiator, there may be used, for example: benzoin alkyl ethers, such as benzoin methyl ether, benzoin ethyl ether, and benzoin isopropyl ether; benzyl ketals, such as benzyl dimethyl ketal and benzyl diethyl ketal; benzophenones, such as benzophenone, 4,4'-dimethylbenzophenone, and 4-methacryloxybenzophenone; α-diketones, such as diacetyl, benzyl 2,3-pentanedione, camphorquinone, 9,10-phenanthraquinone, and 9,10-anthraquinone; thioxanthone compounds, such as 2,4-diethoxythioxanthone, 2-chlorothioxanthone, and methylthioxanthone; and acylphosphine oxides, such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, 2,4,6-trimethylbenzoyldiphenylphosphine oxide, and bis(2,4,6-trimethylbenzoyl)-phenylphosphine oxide.

A reducing agent is often added to the photopolymerization initiator, and examples thereof may include: tertiary amines, such as 2-(dimethylamino)ethyl methacrylate, ethyl 4-dimethylaminobenzoate, and N-methyldiethanolamine; aldehydes, such as lauryl aldehyde, dimethylaminobenzaldehyde, and terephthalaldehyde; and sulfur-containing compounds, such as 2-mercaptobenzoxazole, 1-decanethiol, thiosalicylic acid, and thiobenzoic acid.

In addition, as a thermal polymerization initiator, there are given, for example: peroxides, such as benzoyl peroxide, p-chlorobenzoyl peroxide, tert-butyl peroxy-2-ethylhexanoate, tert-butyl peroxydicarbonate, and diisopropyl peroxydicarbonate; azo compounds, such as azobisisobutyronitrile; boron compounds, such as tributylborane, tributylborane partial oxide, sodium tetraphenylborate, sodium tetrakis(p-fluorophenyl)borate, and triethanolamine tetraphenylborate; barbituric acids, such as 5-butylbarbituric acid and 1-benzyl-5-phenylbarbituric acid; and sulfinates, such as sodium benzenesulfinate and sodium p-toluenesulfinate.

Those polymerization initiators may be used alone or as a mixture thereof. The blending amount of the polymerization initiator only needs to be appropriately decided in consideration of, for example, polymerization activity in the production of (A) the organic-inorganic composite particles and coloring of (A-1) the organic resin, but is preferably from 0.01 part by mass to 5 parts by mass with respect to 100 parts by mass of (a-1) the polymerizable monomer to be used for the formation of (A-1) the organic resin.

Elastic Modulus

In the curable composition according to this embodiment, as shown in the expression (1), it is required that the elastic modulus M of the matrix formed of a portion in the cured body other than (A) the organic-inorganic composite particles be larger than the elastic modulus P of (A) the organic-inorganic composite particles by 3.0 GPa or more, preferably 5 GPa or more, more preferably 6 GPa or more, still more preferably 7 GPa or more. The upper limit of the elastic modulus difference $\Delta$ (elastic modulus M-elastic modulus P) is not particularly limited, but for practical purposes, is preferably 18 GPa or less. When the elastic moduli M and P satisfy the expression (1), a cured product having high fracture energy is obtained. Although the reason why such effect is obtained has yet to be elucidated, the inventors of the present invention have presumed as follows. That is, a possible reason is that, in the cured product obtained by curing the curable composition according to this embodiment, a large number of (A) the organic-inorganic composite particles having a relatively low elastic modulus with respect to that of the matrix are dispersed in the cured body, and hence when a stress is applied to the cured product, each of (A) the organic-inorganic composite particles effectively disperses the applied stress in the system. In addition, in order to obtain the above-mentioned effect, it is only required to prepare (A) the organic-inorganic composite particles, and the composition for forming the matrix (i.e., the components in the curable composition except for (A) the organic-inorganic composite particles, in other words, components including at least (B) the polymerizable monomer, (C) the polymerization initiator, and (D) the inorganic particles) so that the elastic moduli M and P may satisfy the expression (1).

In addition, under the condition that the expression (1) is satisfied, the elastic modulus P of (A) the organic-inorganic composite particles is preferably from 0.01 GPa to 12.0 GPa, and the elastic modulus M of the matrix is preferably from 6.0 GPa to 30.0 GPa. By satisfying the expression (1) and preparing (A) the organic-inorganic composite particles having an elastic modulus P of from 0.01 GPa to 12.0 GPa, even when a stress is applied to the cured body of the curable composition according to this embodiment, the stress is effectively dispersed, and hence the fracture energy of the cured body can be further increased. By satisfying the expression (1) and preparing the components in the curable composition except for (A) the organic-inorganic composite particles so that a matrix showing an elastic modulus M of from 6.0 GPa to 30.0 GPa may be obtained, the brittleness of the cured body of the curable composition according to this embodiment can be suppressed, and hence the fracture energy of the cured body can be further increased. The elastic modulus P is more preferably from 1.0 GPa to 8.5 GPa, still more preferably from 1.5 GPa to 5.0 GPa. The elastic modulus M is more preferably from 10 GPa to 22 GPa, still more preferably from 14 GPa to 20 GPa.

For the control of each of the elastic moduli P and M, it is only required to appropriately prepare each of the constituent components of the curable composition, and a control method for each of the elastic moduli P and M is not particularly limited. A method of adjusting the elastic modulus P of (A) the organic-inorganic composite particles preferably involves controlling the crosslinking density of (A-1) the organic resin, or adjusting the content of (A-2) the inorganic particles. In this case, the elastic modulus P increases as the crosslinking density increases when the crosslinking density of (A-1) the organic resin is controlled, or as the content of the inorganic particles increases when the content of (A-2) the inorganic particles is adjusted. In addition, the elastic modulus P lowers as the crosslinking density lowers or as the content of (A-2) the inorganic particles decreases.

The crosslinking density of (A-1) the organic resin is determined by the number of crosslinking points. In this connection, in the case of (A-1) the organic resin produced using (a-1) the polymerizable monomer as a raw material, a polymerizable functional group contained in (a-1) the polymerizable monomer serves as a crosslinking point. Therefore, a molecular weight per polymerizable functional group contained in (a-1) the polymerizable monomer serves as an indicator for determining the elastic modulus P. That is, when the molecular weight per polymerizable functional group contained in (a-1) the polymerizable monomer is large, the elastic modulus P decreases, and when the molecular weight per polymerizable functional group is small, the elastic modulus P increases.

In this connection, in the description of the present application, the "molecular weight per polymerizable functional group" refers to a value represented by M/n, where M represents the molecular weight of the polymerizable monomer and n represents the number of polymerizable functional groups contained in one molecule of the polymerizable monomer (n represents an integer of 1 or more). In addition, when two or more kinds of polymerizable monomers are used as a mixture, the "molecular weight per polymerizable functional group" means the weighted average value of molecular weights per polymerizable functional group in the respective kinds of polymerizable monomers. In addition, polymerizable functional groups contained in (a-1) the polymerizable monomer and (B) the polymerizable monomer to be described later are not particularly limited as long as the polymerizable functional groups are each a functional group showing polymerizability, but examples thereof include a vinyl group, a styryl group, an allyl group, and a (meth)acryloyl group. As each of (a-1) the polymerizable monomer and (B) the polymerizable monomer to be described later, any polymerizable monomer in which the number of polymerizable functional groups contained in the molecule is 1 or more may be utilized, and a monofunctional (single functional) polymerizable monomer in which the number of polymerizable functional groups contained in the molecule is 1 may be used. However, in order that a crosslinked structure may be easily formed, the number of polymerizable functional groups contained in the molecule is preferably 2 or more (polyfunctional polymerizable monomer), and further, from the viewpoint of a practical purpose, such as the ease of availability, the number of polymerizable functional groups contained in the molecule is most preferably 2 (bifunctional polymerizable monomer). Therefore, as each of (a-1) the polymerizable monomer and (B) the polymerizable monomer to be described later, it is preferred to use only a bifunctional polymerizable monomer. When a bifunctional polymerizable monomer and a p-functional polymerizable monomer (where p represents an integer of 1 or 3 or more) are used as a mixture, the ratio of the bifunctional polymerizable monomer in all polymerizable monomers is preferably 80 mass % or more, more preferably 90 mass % or more.

In this connection, in order to adjust the elastic modulus P of (A) the organic-inorganic composite particles within the range of from 0.01 GPa to 12.0 GPa, (A-1) the organic resin for forming each of (A) the organic-inorganic composite particles is preferably a cured body of (a-1) a polymerizable monomer having a molecular weight per polymerizable functional group contained in the molecule of from 230 to 1,000, more preferably a cured body of (a-1) a polymerizable monomer having a molecular weight per polymerizable functional group contained in the molecule of from 265 to 450, still more preferably a cured body of (a-1) a polymerizable monomer having a molecular weight per polymerizable functional group contained in the molecule of from 350 to 450.

Examples of (a-1) the polymerizable monomer having such molecular weight alone include nonaethylene glycol dimethacrylate (molecular weight: 536, number of polymerizable functional groups: 2, molecular weight per polymerizable functional group: 268), polyethylene glycol #600 dimethacrylate (molecular weight: 736, number of polymerizable functional groups: 2, molecular weight per polymerizable functional group: 368), 2,2-bis[4-(methacryloxypolyethoxy)phenyl]propane (10 mol of EO) (molecular weight: 804, number of polymerizable functional groups: 2, molecular weight per polymerizable functional group: 402), 2,2-bis[4-(methacryloxypolyethoxy)phenyl]propane (17 mol of EO) (molecular weight: 1,112, number of polymerizable functional groups: 2, molecular weight per polymerizable functional group: 556), ethoxylated polypropylene glycol #700 dimethacrylate (molecular weight: 1,114, number of polymerizable functional groups: 2, molecular weight per polymerizable functional group: 557), polyethylene glycol #600 diacrylate (molecular weight: 708, number of polymerizable functional groups: 2, molecular weight per polymerizable functional group: 354), 2,2-bis[4-(acryloxypolyethoxy)phenyl]propane (10 mol of EO) (molecular weight: 776, number of polymerizable functional groups: 2, molecular weight per polymerizable functional group: 388), and polypropylene glycol #650 diacrylate (molecular weight: 758, number of polymerizable functional groups: 2, molecular weight per polymerizable functional group: 379). In the description of the present application, "EO" means a repeating unit: —($CH_2CH_2O$)— contained in the molecule of the polymerizable monomer, and the number of moles of EO shown in parentheses means the number of moles per 1 mol of the polymerizable monomer. When two or more kinds of polymerizable monomers different from each other in molecular weight per polymerizable functional group contained in the molecule are used as (a-1) the polymerizable monomer, the two or more kinds of polymerizable monomers are preferably used as a blend so that the weighted average value of molecular weights per polymerizable functional group contained in the molecule of the respective kinds of polymerizable monomers may be from 230 to 1,000, more preferably from 265 to 450, still more preferably from 350 to 450. In the description of the present application, a value measured by mass spectrometry is used for a molecular weight.

(A-2) Inorganic Particles

A material for (A-2) the inorganic particles for forming (A) the organic-inorganic composite particles is not particularly limited, and any inorganic particles that have been used as a filler for a related-art curable composition may be used. Specific examples thereof include simple substances of metals selected from Groups I, II, III, and IV of the periodic table and transition metals, oxides and composite oxides of those metals, metal salts, such as fluorides, carbonates, sulfates, silicates, hydroxides, chlorides, sulfites, and phosphates, and composites of those metal salts. There may be suitably adopted, for example: metal oxides, such as amorphous silica, quartz, alumina, titania, zirconia, barium oxide, yttrium oxide, lanthanum oxide, and ytterbium oxide; silica-based composite oxides, such as silica-zirconia, silica-titania, silica-titania-barium oxide, and silica-titania-zirconia; glasses, such as borosilicate glass, aluminosilicate glass, and fluoroaluminosilicate glass; metal fluorides, such as barium fluoride, strontium fluoride, yttrium fluoride, lanthanum fluoride, and ytterbium fluoride; inorganic carbonates, such as calcium carbonate, magnesium carbonate, strontium carbonate, and barium carbonate; and metal sulfates, such as magnesium sulfate and barium sulfate.

Of those, metal oxides and silica-based composite oxides are each preferably a product of firing at high temperature in order to provide a dense material. In order to improve such effect, a small amount of an oxide of a metal of Group I of the periodic table, such as sodium, is preferably incorporated.

Of inorganic particles of the above-mentioned materials, silica-based composite oxide particles are easy to adjust for its refractive index. Further, the silica-based composite oxide particles have a large amount of silanol groups on its particle surface, and hence are easy to surface-modify using a silane coupling agent or the like. Therefore, the silica-based composite oxide particles are particularly preferred.

The particles of silica-zirconia, silica-titania, silica-titania-barium oxide, silica-titania-zirconia, and the like given as examples above are each suitable because of having a strong X-ray contrast property. Further, silica-zirconia particles are most preferred because a cured body more excellent in wear resistance is obtained.

The average particle diameter of primary particles of (A-2) the inorganic particles for forming (A) the organic-inorganic composite particles is not particularly limited as long as the particle diameter is smaller than that of (A) the organic-inorganic composite particles. However, from the viewpoint that the glossiness and mechanical strength of the cured body of the curable composition to be obtained can be increased, the average particle diameter is preferably from 10 nm to 1,000 nm, more preferably from 40 nm to 800 nm, most preferably from 50 nm to 600 nm. In addition, with regard to the shape of (A-2) the inorganic particles, inorganic particles having a spherical shape are particularly suitably used because a cured body of a curable composition particularly excellent in wear resistance, surface smoothness, and gloss retention is obtained.

In the description of the present application, the average particle diameter of (A-2) the inorganic particles refers to the circle-equivalent diameter of a primary particle diameter (the diameter of a circle having the same area as the area of a particle of interest) measured by image analysis on the basis of an image taken with a scanning electron microscope or a transmission electron microscope. As the image taken with an electron microscope to be used for the measurement, an image having a clear contrast and allowing the contour of each of the particles to be recognized is used. As a method for the image analysis, the image analysis is performed using image analysis software capable of measuring at least the area of a particle and the maximum length and minimum length of a particle. Herein, the average particle diameter and average degree of symmetry of the primary particles of (A-2) the inorganic particles are calculated by the following equations using the primary particle diameters of individual particles obtained using the electron microscope and image analysis described above.

Average particle diameter:

$$X = \sqrt[3]{\frac{\sum_{i=1}^{n} X_i^3}{n}}$$

n: number of observed particles
Xi: particle diameter (diameter) of i-th particle $$\text{Average degree of symmetry} = \frac{\sum_{i=1}^{n} \frac{Bi}{Li}}{n}$$

In the equation for determining the average particle diameter and the equation for determining the average degree of symmetry, i represents an integer of 1 or more, and n represents the number of particles sampled as measurement objects (number of observed particles). In addition, in the equation for determining the average degree of symmetry, Li represents the maximum length (long diameter) of an i-th particle, and Bi represents the diameter (minimum length, short diameter) of the i-th particle in a direction orthogonal to the long diameter Li. When the average particle diameter and the average degree of symmetry are calculated, 40 particles are sampled and subjected to measurement.

Production Method for (A-2) Inorganic Particles (A-2) The inorganic particles may be inorganic particles produced by any known method. For example, in the case of using an inorganic oxide, a composite oxide, or the like, (A-2) the inorganic particles may be produced by any method out of a wet method, a dry method, and a sol-gel method. In consideration of: an advantage in industrial production of fine particles having a spherical shape and excellent in monodispersity; and the ease with which the refractive index is adjusted or an X-ray contrast property is imparted, (A-2) the inorganic particles are preferably produced by a sol-gel method.

As a method of producing spherical silica-based composite oxide particles serving as (A-2) the inorganic particles by a sol-gel method, a production method disclosed in, for example, JP 58-110414 A, JP 58-151321 A, JP 58-156524 A, or JP 58-156526 A, may be utilized.

In this production method, first, a raw material solution containing a hydrolyzable organic silicon compound, or a raw material solution formed of a mixed solution obtained by further adding, to the above-mentioned raw material solution, a hydrolysable organic metal compound containing a metal other than silicon is prepared. Next, the raw material solution is added into an alkaline solvent capable of dissolving the organic silicon compound and organic metal compound contained in the raw material solution but substantially incapable of dissolving an inorganic oxide that is a product, to thereby perform hydrolysis treatment to precipitate the inorganic oxide. The precipitate is separated by filtration, and then the precipitate is dried.

The inorganic particles obtained by such method may be fired at a temperature of from 500° C. to 1,000° C. after the drying in order to impart surface stability thereto. During the firing, part of the inorganic particles may be aggregated to form aggregated particles. In this case, it is preferred that the aggregated particles be broken down into primary particles using a jet mill, a vibration ball mill, or the like and their particle sizes be further adjusted to a predetermined range before use. The curable composition according to this embodiment using (A-2) the inorganic particles obtained through such treatment is improved in, for example, polishability of its cured body. Accordingly, (A-2) the inorganic particles obtained through such treatment are more suitable in the use of the curable composition according to this embodiment as a curable composition for dental use. As (A-2) the inorganic particles, a mixture of a plurality of inorganic particles different from each other in average particle diameter, material, or shape may be used.

Surface Treatment of (A-2) Inorganic Particles (A-2) The inorganic particles to be used for (A) the organic-inorganic composite particles are preferably subjected to surface treatment with a hydrophobizing agent in order to improve wettability to (a-1) the polymerizable monomer.

A conventionally known hydrophobizing agent is used as the hydrophobizing agent without any limitation. Suitable examples of the hydrophobizing agent include: silane coupling agents, such as vinyltriethoxysilane, vinyltrimethoxysilane, vinyl-tris(β-methoxyethoxy)silane, γ-methacryloyloxypropyltrimethoxysilane, κ-methacryloyloxydodecyltrimethoxysilane, β-(3,4-epoxycyclohexyl)-ethyltrimethoxysilane, γ-glycidoxypropyltrimethoxysilane, N-β-(aminoethyl)-γ-aminopropyltrimethoxysilane, γ-ureidopropyl-triethoxysilane, γ-chloropropyltrimethoxysilane, methyltrimethoxysilane, ethyltrimethoxysilane, and methyltriethoxysilane; and titanate-based coupling agents.

The use amount of the hydrophobizing agent to be used for the hydrophobization of (A-2) the inorganic particles is not particularly limited, and a suitable use amount of the hydrophobizing agent is, for example, from 1 part by mass to 30 parts by mass of the hydrophobizing agent with respect to 100 parts by mass of (A-2) the inorganic particles.

A method for the surface treatment is not particularly limited, and a known method may be adopted without any limitation. As a typical treatment method, for example, there is given a method involving dispersing and mixing (A-2) the inorganic particles and the hydrophobizing agent in an appropriate solvent through the use of a ball mill or the like, drying the resultant with an evaporator or by air drying, and then heating the resultant to from 50° C. to 150° C. There is also given a method involving heating (A-2) the inorganic particles and the hydrophobizing agent under reflux in a solvent, such as an alcohol, for about several hours. There is also given, for example, a method involving subjecting the hydrophobizing agent to graft polymerization on the surface of the particles.

The surface treatment may be performed on (A-2) the inorganic particles, or may be performed on inorganic aggregated particles obtained by aggregating (A-2) the inorganic particles. When the inorganic aggregated particles are produced by a spray-drying method, it is efficient to simultaneously perform, during this treatment, the surface treatment. A production method for the inorganic aggregated particles is described later.

Blending Ratio of (A-1) Organic Resin and (A-2) Inorganic Particles

The content of (A-1) the organic resin in (A) the organic-inorganic composite particles is preferably from 1 part by mass to 40 parts by mass, more preferably from 5 parts by mass to 25 parts by mass with respect to 100 parts by mass of (A-2) the inorganic particles because the fracture energy of the cured body of the curable composition is increased and (A-2) the inorganic particles are easily dispersed in (A-1) the organic resin. The content of (A-1) the organic resin in (A) the organic-inorganic composite particles may be determined from a weight loss in differential thermal-thermogravimetric simultaneous measurement.

Particle Diameter of (A) Organic-inorganic Composite Particles

The particle diameter of (A) the organic-inorganic composite particles is not limited, but in order that a cured body having high fracture energy may be easily obtained, the average particle diameter of (A) the organic-inorganic composite particles is preferably from 1 μm to 50 μm, more preferably from 7 μm to 16 μm. When the average particle diameter of (A) the organic-inorganic composite particles is set to fall within the above-mentioned range, an increase in viscosity of the curable composition and nonuniformization thereof are suppressed, resulting in improved workability of the curable composition. Consequently, lowering of the fracture energy of the cured body due to a trouble in work, such as inclusion of air bubbles in the curable composition, can be prevented. The average particle diameter of (A) the organic-inorganic composite particles is measured as a median diameter determined on the basis of a particle size distribution according to a laser diffraction-scattering method. A sample to be subjected to the measurement is prepared by uniformly dispersing 0.1 g of (A) the organic-inorganic composite particles in 10 mL of ethanol.

Shape of (A) Organic-inorganic Composite Particles

The shape of (A) the organic-inorganic composite particles is not particularly limited, but is preferably spherical or substantially spherical because, when a stress is applied to a cured body of the curable composition according to this embodiment, the stress is uniformly dispersed on the surface of (A) the organic-inorganic composite particles, to thereby facilitate the increase of the fracture energy of the cured body. As used herein, the term "substantially spherical" means that the average degree of symmetry of the surfaces of (A) the organic-inorganic composite particles determined in image analysis of an image taken with a scanning electron microscope or a transmission electron microscope is 0.6 or more. The average degree of symmetry is more preferably 0.7 or more, still more preferably 0.8 or more. The average degree of symmetry is measured using a scanning electron microscope or a transmission electron microscope. Specifically, through image analysis of an image taken of (A) the organic-inorganic composite particles, the average degree of symmetry is determined from the maximum lengths and minimum lengths of (A) the organic-inorganic composite particles. As the image taken with an electron microscope, an image having a clear contrast and allowing the contour of each of the particles to be recognized is used. The image analysis is performed using image analysis software capable of measuring at least the maximum length and minimum length of a particle. For 100 randomly selected (A) organic-inorganic composite particles, the maximum length and minimum length of each particle are determined by the above-mentioned method, and the average degree of symmetry of (A) the organic-inorganic composite particles is calculated by the following equation.

$$\text{Average degree of symmetry} = \frac{\sum_{i=1}^{n} \frac{Bi}{Li}}{n}$$

In the equation, i represents an integer of 1 or more, and n represents the number of particles sampled as measurement objects. In addition, Li represents the maximum length (long diameter) of an i-th particle, and Bi represents the diameter (minimum length, short diameter) of the i-th particle in a direction orthogonal to the long diameter Li.

Micropore Volume of (A) Organic-inorganic Composite Particles (A) The organic-inorganic composite particles may be porous particles having micropores, or may be non-porous particles (particles each having a dense structure). When (A) the organic-inorganic composite particles have micropores, (A) the organic-inorganic composite particles preferably have micropores at least in the vicinity of the surfaces of the particles, and may have micropores throughout the particles. For example, (A) the organic-inorganic composite particles having micropores may be obtained by allowing (a-1) the polymerizable monomer to penetrate aggregation gaps of inorganic aggregated particles formed of aggregates of (A-2) the inorganic particles, and then polymerizing and curing (a-1) the polymerizable monomer. In order to obtain a cured body having even higher fracture energy from a curable composition using such (A) organic-inorganic composite particles having micropores, the micropore volume of (A) the organic-inorganic composite particles having micropores is preferably from $0.01 \text{ cm}^3/\text{g}$ to $0.30 \text{ cm}^3/\text{g}$, more preferably from $0.03 \text{ cm}^3/\text{g}$ to $0.20 \text{ cm}^3/\text{g}$, still more preferably from $0.05 \text{ cm}^3/\text{g}$ to $0.15 \text{ cm}^3/\text{g}$.

In the curable composition using (A) the organic-inorganic composite particles having micropores having a micropore volume of from $0.01 \text{ cm}^3/\text{g}$ to $0.30 \text{ cm}^3/\text{g}$, (B) the polymerizable monomer contained in the curable composition penetrates the micropores due to capillarity and is then cured, with the result that an anchoring effect occurs. Accordingly, it is presumed that (A) the organic-inorganic composite particles having micropores are retained in the cured body of the curable composition with high interlocking strength, resulting in an improvement in mechanical strength of the cured body. In addition to the foregoing, (A) the organic-inorganic composite particles having micropores have micropores formed at least in the vicinity of the surfaces of the particles, and hence, in the cured body, an interfacial area between each of (A) the organic-inorganic composite particles having micropores and the matrix present on the peripheries of (A) the organic-inorganic composite particles having micropores is increased. Accordingly, it is considered that a stress applied to the cured body is more effectively dispersed, resulting in a further improvement in fracture energy of the cured body. In the description of the present application, the term "micropores" means pores having a micropore diameter, which can be measured by a nitrogen adsorption method, in the range of from 1 nm to 500 nm. In addition, the micropore volume may be determined by calculating a micropore diameter distribution by a BJH method based on an isothermal adsorption curve measured by a BET method based on nitrogen adsorption.

Production Method for Organic-inorganic Composite Particles

A production method for (A) the organic-inorganic composite particles to be used for the curable composition according to this embodiment is not particularly limited, and may be arbitrarily selected. For example, (A) the organic-inorganic composite particles may be obtained by: dispersing and mixing (A-2) the inorganic particles in (A-1) the organic resin in a liquid form, solidifying the resultant to prepare an agglomerated organic-inorganic composite, and then pulverizing and classifying the agglomerated organic-inorganic composite; dispersing and mixing (A-2) the inorganic particles in (a-1) the polymerizable monomer, polymerizing and curing the resultant to prepare an agglomerated organic-inorganic composite, and then pulverizing and classifying the agglomerated organic-inorganic composite; or impregnating inorganic aggregated particles formed of aggregates of (A-2) the inorganic particles with (a-1) the polymerizable monomer, and then solidifying or polymerizing and curing the resultant. As a method of allowing (a-1) the polymerizable monomer to penetrate the inorganic aggregated particles, there is given a method involving immersing the inorganic aggregated particles in a polymerizable monomer solution. As an organic solvent to be contained in the polymerizable monomer solution, a known solvent may be used without any limitation, but an alcohol-based solvent, such as methanol or ethanol, acetone, dichloromethane, or the like is preferably used from the viewpoints of, for example, having high volatility for allowing easy removal of the solvent, being easily available and inexpensive, and being highly safe for the human body during production. As a polymerization initiator to be contained in the polymerizable monomer solution, the same polymerization initiator as the above-mentioned polymerization initiator may be used. As the polymerization initiator to be used, a photopolymerization initiator or a thermal polymerization initiator is preferred because the timing of polymerization can be arbitrarily selected on the basis of the energy to be externally applied and the operation is simple, and a thermal polymerization initiator is more preferred because the thermal polymerization initiator can be used without restricting a working environment to being, for example, a light-shielding condition or under red light. When the inorganic aggregated particles are immersed in the polymerizable monomer solution, it is generally preferred that the immersion be performed under ordinary temperature and ordinary pressure. A mixing ratio between the inorganic aggregated particles and the polymerizable monomer solution is preferably from 30 parts by mass to 500 parts by mass, more preferably from 50 parts by mass to 200 parts by mass of the polymerizable monomer solution with respect to 100 parts by mass of the inorganic aggregated particles so that the blending ratio of (A-1) the organic resin may be from 1 part by mass to 40 parts by mass with respect to 100 parts by mass of (A-2) the inorganic particles in (A) the organic-inorganic composite particles. In order to allow the polymerizable monomer to sufficiently penetrate the inside of the inorganic aggregated particles, a mixture obtained by mixing the inorganic aggregated particles and the polymerizable monomer solution is preferably left to stand still after the mixing. A temperature at which the mixture is left to stand still is not particularly limited, but is generally room temperature. A period of time for which the mixture is left to stand still is preferably 30 minutes or more, more preferably 1 hour or more. In order to promote the penetration of the polymerizable monomer solution into the aggregation gaps of the inorganic aggregated particles, the mixture of the polymerizable monomer solution and the inorganic aggregated particles may be subjected to stirring by shaking, centrifugal stirring, pressurization, reduced pressure, or heating.

After the immersion of the polymerizable monomer solution into the aggregation gaps of the inorganic aggregated particles, the organic solvent is removed from the polymerizable monomer solution. In the removal of the organic solvent, substantially the whole amount (generally 95 mass % or more) of the organic solvent penetrating the inorganic aggregated particles is removed. Visually, the removal only needs to be performed until there is no solidified product formed by adhesion of the inorganic aggregated particles to each other and fluid powder is obtained. Any known drying operation may be performed as an operation for removing the organic solvent, but in order to shorten a drying time, a method involving performing drying by heating under reduced pressure is preferred. A degree of reduction in pressure and a drying temperature only need to be appropriately selected in consideration of the volatility and boiling point of the organic solvent to be removed. After the removal of the organic solvent, the polymerizable monomer is polymerized and cured, and thus (A) the organic-inorganic composite particles are prepared. (A) Organic-inorganic composite particles having a predetermined micropore volume may be produced in accordance with a known method (e.g., WO 2013/039169 A1).

Surface Treatment of (A) Organic-inorganic Composite Particles (A) The organic-inorganic composite particles may be subjected to surface treatment. When the surface treatment is performed, higher mechanical strength is imparted to the cured body of the curable composition having blended therein the resultant organic-inorganic composite particles. A hydrophobizing agent to be used for the surface treatment and a method for the surface treatment are the same as those for the surface treatment of (A-2) the inorganic particles described above.

Blending Amount of (A) Organic-inorganic Composite Particles in Curable Composition The blending amount of (A) the organic-inorganic composite particles in the curable composition is preferably from 50 parts by mass to 500 parts by mass, preferably from 100 parts by mass to 300 parts by mass with respect to 100 parts by mass of (B) the polymerizable monomer. When such blending amount is adopted, a stress applied to the cured body of the curable composition according to this embodiment can be more effectively dispersed, and hence it is easy to further improve the fracture energy.

(B) Polymerizable Monomer (B) The polymerizable monomer to be used for the curable composition according to this embodiment is a main component for forming the matrix that is present so as to surround the peripheries of (A) the organic-inorganic composite particles, and a known polymerizable monomer may be used. As (B) the polymerizable monomer, the same kind of polymerizable monomer as (a-1) the polymerizable monomer to be used for the formation of (A-1) the organic resin may be used. In addition, (B) the polymerizable monomers may be used alone or in combination thereof.

In the cured body obtained by curing the curable composition according to this embodiment, it is required that the elastic modulus M of the matrix constituting a portion other than (A) the organic-inorganic composite particles be larger than the elastic modulus P of (A) the organic-inorganic composite particles by 3.0 GPa or more, preferably 5 GPa or more, more preferably 6 GPa or more, still more preferably 7 GPa or more. The upper limit of the elastic modulus difference A (elastic modulus M-elastic modulus P) is not particularly limited, but for practical purposes, is preferably 18 GPa or less. The elastic moduli M and P only need to be appropriately adjusted on the basis of the kind and blending amount of each of the constituent components of the curable composition, and a method for the adjustment is not particularly limited.

As a method of adjusting the elastic modulus M of the matrix, a method involving controlling the crosslinking density of the resin component for forming the matrix, or a method involving adjusting the content of (D) the inorganic particles is preferably adopted. The elastic modulus M increases as the crosslinking density increases when the crosslinking density of the resin component for forming the matrix is controlled, or as the content of (D) the inorganic particles increases when the content of (D) the inorganic particles is adjusted. In addition, the elastic modulus M lowers as the crosslinking density lowers or as the content of (D) the inorganic particles decreases.

The crosslinking density of the resin component for forming the matrix is determined by the number of crosslinking points. In this connection, in a resin component formed using (B) the polymerizable monomer as a raw material, a polymerizable functional group contained in (B) the polymerizable monomer serves as a crosslinking point. Therefore, the molecular weight per polymerizable functional group contained in (B) the polymerizable monomer serves as an indicator for determining the elastic modulus M. That is, when the molecular weight per polymerizable functional group contained in (B) the polymerizable monomer is large, the elastic modulus M decreases, and when the molecular weight per polymerizable functional group is small, the elastic modulus M increases.

In this connection, in order to adjust the elastic modulus M of the matrix within the range of from 6.0 GPa to 30.0 GPa, the resin component for forming the matrix is preferably a cured body of (B) a polymerizable monomer having a molecular weight per polymerizable functional group contained in the molecule of less than 265, more preferably a cured body of (B) a polymerizable monomer having a molecular weight per polymerizable functional group contained in the molecule of from 35 to 250, still more preferably a cured body of (B) a polymerizable monomer having a molecular weight per polymerizable functional group contained in the molecule of from 100 to 210, particularly preferably a cured body of (B) a polymerizable monomer having a molecular weight per polymerizable functional group contained in the molecule of from 160 to 210.

Examples of (B) the polymerizable monomer having such molecular weight alone include triethylene glycol dimethacrylate (molecular weight: 286, number of polymerizable functional groups: 2, molecular weight per polymerizable functional group: 143), 2,2-bis[4(2-hydroxy-3-methacryloyloxypropoxy)phenyl]propane) (molecular weight: 513, number of polymerizable functional groups: 2, molecular weight per polymerizable functional group: 257), 2,2-bis[4-(methacryloxypolyethoxy)phenyl]propane (2.6 mol of EO) (molecular weight: 478, number of polymerizable functional groups: 2, molecular weight per polymerizable functional group: 239), 1,6-bis(methacryloyloxy-2-ethoxycarbonylamino)-2,4,4-trimethyl hexane (molecular weight: 470, number of polymerizable functional groups: 2, molecular weight per polymerizable functional group: 235), 1,4-butanediol dimethacrylate (molecular weight: 226, number of polymerizable functional groups: 2, molecular weight per polymerizable functional group: 113), 1,6-hexanediol dimethacrylate (molecular weight: 254, number of polymerizable functional groups: 2, molecular weight per polymerizable functional group: 127), tricyclodecane dimethanol dimethacrylate (molecular weight: 332, number of polymerizable functional groups: 2, molecular weight per polymerizable functional group: 166), and trimethylolpropane trimethacrylate (molecular weight: 338, number of polymerizable functional groups: 3, molecular weight per polymerizable functional group: 113). When two or more kinds of polymerizable monomers different from each other in molecular weight per polymerizable functional group contained in the molecule are used as (B) the polymerizable monomer, the two or more kinds of polymerizable monomers are preferably used as a blend so that the weighted average value of molecular weights per polymerizable functional group contained in the molecule of the respective kinds of polymerizable monomers may be less than 265, more preferably from 35 to 250, still more preferably from 100 to 210, most preferably from 160 to 210.

(C) Polymerization Initiator

The curable composition according to this embodiment has added thereto (C) the polymerization initiator in order to promote the polymerization and curing of (B) the polymerizable monomer. As (C) the polymerization initiator, the same kind of polymerization initiator as the polymerization initiator to be used for the polymerization of (a-1) the polymerizable monomer in the formation of (A-1) the organic resin for forming each of (A) the organic-inorganic composite particles may be used. In addition, (C) the polymerization initiators may be used alone or in combination thereof. The blending amount of (C) the polymerization initiator only needs to be appropriately decided in consideration of, for example, polymerization activity and the coloring of the cured body, but is preferably from 0.01 part by mass to 5 parts by mass with respect to 100 parts by mass of (B) the polymerizable monomer.

(D) Inorganic Particles

The curable composition according to this embodiment has blended therein (D) the inorganic particles from the viewpoints of, for example, an improvement in wear resistance of the cured body, improvements in mechanical physical properties thereof, a reduction in thermal expansion coefficient thereof, a reduction in water-absorbing property thereof, and a reduction in solubility thereof. (D) The inorganic particles are dispersed in (B) the polymerizable monomer. (B) The polymerizable monomer and (D) the inorganic particles form the matrix that surrounds (A) the organic-inorganic composite particles after the curing of the curable composition. In addition, the blending amount of (D) the inorganic particles influences the elastic modulus M of the matrix.

As (D) the inorganic particles, known inorganic particles may be used without any limitation. As (D) the inorganic particles, the same inorganic particles as (A-2) the inorganic particles for forming (A) the organic-inorganic composite particles described above may be used. Of those, a composite oxide using, as main constituent components, silica and zirconia, silica and titania, or silica and barium oxide is preferably used because the composite oxide has a high X-ray contrast property. In addition, the shape of (D) the inorganic particles is particularly preferably a spherical shape because a cured body of a curable composition particularly excellent in wear resistance, surface smoothness, and gloss retention is obtained. The average particle diameter of (D) the inorganic particles is preferably from 0.001 μm to 1 μm, and is more preferably from 0.01 μm to 0.5 μm from the viewpoints of the wear resistance, surface smoothness, and gloss retention of the cured body.

The blending amount of (D) the inorganic particles only needs to be selected depending on purposes, but in order that the elastic modulus M of the matrix may be easily adjusted to from 6.0 GPa to 30.0 GPa, (D) the inorganic particles are generally preferably used at a ratio of from 50 parts by mass to 500 parts by mass, more preferably used at a ratio of from 100 parts by mass to 300 parts by mass with respect to 100 parts by mass of (B) the polymerizable monomer.

In order to further increase the mechanical strength, such as fracture energy, of the cured body obtained by curing the curable composition according to this embodiment, it is preferred that: (A-1) the organic resin for forming each of (A) the organic-inorganic composite particles be a cured body of (a-1) a polymerizable monomer having a molecular weight per polymerizable functional group contained in the molecule of from 230 to 1,000; and a molecular weight per polymerizable functional group contained in (B) the polymerizable monomer be from 35 to 250. As each of (a-1) the polymerizable monomer and (B) the polymerizable monomer, a known polymerizable monomer may be used, and as described above, the polymerizable monomers may be appropriately selected from those exemplified as specific examples of (a-1) the polymerizable monomer. (a-1) The polymerizable monomers may be used alone or in combination thereof, and (B) the polymerizable monomers may be used alone or in combination thereof.

Other Optional Components

The curable composition according to this embodiment may further include any other component, as required, in addition to (A) the organic-inorganic composite particles, (B) the polymerizable monomer, (C) the polymerization initiator, and (D) the inorganic particles. Examples of the other component include a filler, a polymerization inhibitor, a fluorescent agent, an ultraviolet absorber, an antioxidant, a pigment, an antibacterial agent, and an X-ray contrast agent other than the components (A) to (D). In addition, (A) the organic-inorganic composite particles only need to contain at least (A-1) the organic resin and (A-2) the inorganic particles, but may further contain the above-mentioned other component as required.

Preparation Method for Curable Composition

The curable composition according to this embodiment may be obtained by weighing and sufficiently kneading predetermined amounts of only the components (A) to (D), or the components (A) to (D) and any other component to be used as required to provide a kneaded product as a paste, and then further degassing the kneaded product to remove air bubbles.

Applications of Curable Composition, Cured Body Thereof, and Organic-Inorganic Composite Particles to be Used for Curable Composition Applications of the curable composition according to this embodiment and the cured body obtained by curing the curable composition are not particularly limited, and the curable composition and the cured body may be used for a mechanical part, an adhesive, a sealing material, and the like. However, because the curable composition according to this embodiment easily provides a cured body having high fracture energy, the curable composition according to this embodiment and the cured body obtained by curing the curable composition are particularly suitably used in dental applications or as dental materials. In this case, a curable composition for dental use formed of the curable composition according to this embodiment may be utilized as a composite resin, a dental restoration material, such as cement, or a raw material composition for producing any of various prostheses for dental use (e.g., a hard resin, an artificial tooth, and a resin material for machining processing).

When the curable composition according to this embodiment is used as a curable composition for dental use, a cured product thereof is generally used in an oral cavity over a long period of time. That is, a cured product to be utilized as a dental material is required to have, for example, mechanical strength and durability against a stress to be repeatedly applied at the time of occluding, water resistance against water in saliva or the like, and safety for a living body. A curable composition to be utilized as a dental material is required to have excellent workability in order to facilitate working in an oral cavity at the time of dental treatment, to thereby reduce a burden on a dentist, a dental technician, or a patient. Therefore, from the viewpoint of securing the mechanical strength and durability, with regard to the blending amount of (D) the inorganic particles, (D) the inorganic particles are preferably used at a ratio of from 50 parts by mass to 500 parts by mass, preferably used at a ratio of from 100 parts by mass to 300 parts by mass with respect to 100 parts by mass of (B) the polymerizable monomer. In addition, with regard to the total blending amount of (A) the organic-inorganic composite particles and (D) the inorganic particles, (A) the organic-inorganic composite particles and (D) the inorganic particles are preferably used at a ratio of from 100 parts by mass to 1,000 parts by mass, preferably used at a ratio of from 200 parts by mass to 600 parts by mass with respect to 100 parts by mass of (B) the polymerizable monomer. In addition, from the viewpoint of the safety for a living body, the polymerizable functional group contained in (B) the polymerizable monomer is preferably formed only of a (meth)acryloyl group, and this point similarly applies to the case in which (A-1) the organic resin for forming each of (A) the organic-inorganic composite particles is formed using (a-1) the polymerizable monomer.

In addition, from the viewpoints of securing the mechanical strength and durability against a stress to be repeatedly applied to the cured body of the curable composition for dental use arranged in an oral cavity, and the water resistance against water in saliva or the like, it is preferred that the number of polymerizable functional groups contained in (B) the polymerizable monomer per molecule be two or more allowing crosslinking at the time of polymerization. In addition, in order that the brittleness of the cured body of the curable composition for dental use may be alleviated, it is preferred that, as (B) the polymerizable monomer, only a bifunctional polymerizable monomer be used, or a mixture of a bifunctional polymerizable monomer and a p-functional polymerizable monomer (where p represents an integer of 1 or 3 or more) be used. These points similarly apply to the case in which (A-1) the organic resin for forming each of (A) the organic-inorganic composite particles is formed using (a-1) the polymerizable monomer.

In addition, from the viewpoint of facilitating working in an oral cavity at the time of dental treatment, particularly when the curable composition according to this embodiment is used as a composite resin or a hard resin, a photopolymerization initiator is preferably used as (C) the polymerization initiator, and (D) the inorganic particles are preferably a silica-based composite oxide because of the ease of surface modification with a silane coupling agent, and are preferably a composite oxide containing a heavy metal element, such as zirconia, barium, or ytterbium, because of having an X-ray contrast property. When the cured product of the curable composition according to this embodiment is used as a resin material for machining processing, a thermal polymerization initiator is preferably used as (C) the polymerization initiator because of having a high polymerization depth and allowing even an inner portion to be cured reliably, and a thermal polymerization initiator formed of a peroxide is particularly preferably used. The dental-use hard resin and resin material for machining processing are each required to have high fracture energy because of their frequent use in a site to which relatively high occlusal pressure is applied, or for restoring a relatively large defect, and hence are particularly preferred as applications of the curable composition according to this embodiment. When the curable composition according to this embodiment is used as cement, a chemical polymerization initiator formed of a combination of two or more kinds of components is preferably used as (C) the polymerization initiator because of being able to be used in an oral cavity, and having a high polymerization depth and allowing even an inner portion to be cured reliably. In this case, the cement is formed of a first agent containing at least one kind of constituent component of the chemical polymerization initiator and a second agent containing the remaining constituent component(s) of the chemical polymerization initiator, and the first agent and the second agent are mixed when the cement is used.

In addition, (A) the organic-inorganic composite particles to be used for the curable composition according to this embodiment are suitably used as an organic-inorganic composite particle for dental use. In this case, the organic-inorganic composite particle for dental use is used for a curable composition for dental use (in particular, a dental restoration material) formed of the curable composition according to this embodiment, and it is preferred that: the organic-inorganic composite particle for dental use ((A) the organic-inorganic composite particles) have an elastic modulus P of from 0.01 GPa to 12.0 GPa; and a matrix formed by curing components in the curable composition except for (A) the organic-inorganic composite particles have an elastic modulus M of from 6.0 GPa to 30.0 GPa. A cured body obtained by curing a curable composition for dental use using the above-mentioned organic-inorganic composite particle for dental use has high fracture energy.

EXAMPLES

The present invention is more specifically described below by way of Examples, but the present invention is not limited to Examples described below. Materials, testing methods, and the like used in Examples and Comparative Examples are shown below.

(B) Polymerizable Monomer
BMPEPP10: 2,2-bis[4-(methacryloxypolyethoxy)phenyl] propane (10 mol of EO) (molecular weight: 804, number of polymerizable functional groups: 2, molecular weight per polymerizable functional group: 402)
BMPEPP2.6: 2,2-bis[4-(methacryloxypolyethoxy)phenyl] propane (2.6 mol of EO) (molecular weight: 478, number of polymerizable functional groups: 2, molecular weight per polymerizable functional group: 239)
UDMA: 1,6-bis(methacryloyloxy-2-ethoxycarbonylamino)-2,4,4-trimethyl hexane (molecular weight: 470, number of polymerizable functional groups: 2, molecular weight per polymerizable functional group: 235)
TEGDMA: triethylene glycol dimethacrylate (molecular weight: 286, number of polymerizable functional groups: 2, molecular weight per polymerizable functional group: 143)
bis-GMA: 2,2-bis[4(2-hydroxy-3-methacryloyloxypropoxy) phenyl]propane) (molecular weight: 513, number of polymerizable functional groups: 2, molecular weight per polymerizable functional group: 257)
TMPT: trimethylolpropane trimethacrylate (molecular weight: 338, number of polymerizable functional groups: 3, molecular weight per polymerizable functional group: 113)
(C) Polymerization Initiator
BPO: benzoyl peroxide
CQ: camphorquinone
DMBE: dimethylaminobenzoic acid ethyl ester
(D) Inorganic Particles (and Inorganic Aggregated Particles Thereof)
D-1: γ-methacryloyloxypropyltrimethoxysilane-treated product of spherical silica-zirconia having an average particle diameter of 0.15 µm (inorganic aggregated particles are aggregates in which a large number of inorganic particles D-1 are aggregated)

The inorganic particles D-1 (and inorganic aggregated particles thereof) were produced by the following procedure. First, 100 g of spherical silica-zirconia having an average particle diameter of 0.15 µm was added to 200 g of water, and through the use of SC Mill (manufactured by Mitsui Mining Co., Ltd.), an inorganic particle dispersion having dispersed therein spherical silica-zirconia was obtained. Then, 4 g of γ-methacryloyloxypropyltrimethoxysilane and 0.003 g of acetic acid were added to 80 g of water, and the mixture was stirred for 1 hour and 30 minutes to provide a uniform solution having a pH of 4. The solution was added to the inorganic particle dispersion, and the contents were uniformly mixed to provide a mixed liquid having dispersed therein the inorganic particles D-1. The mixed liquid having dispersed therein the inorganic particles D-1 was dried with a spray drier, specifically Spray Drier TSR-2W (manufactured by Sakamotogiken Co., Ltd.), while being gently stirred. The temperature of drying ambient air was 200° C. A solid obtained by the drying was vacuum-dried at 60° C. for 18 hours. Thus, spray-dried aggregates (inorganic aggregated particles) in a state in which the inorganic particles D-1 were aggregated were obtained. A shear force to be applied when the spray-dried aggregates of the inorganic particles D-1 are kneaded with other components causes the inorganic particles D-1 in the aggregated state to be easily crushed into individual primary particles independent of each other.

(1) Elastic Modulus
Measurement was performed with a nanoindentation hardness tester. Under a measurement environment having a temperature of 23° C. and a relative humidity of 50%, a test was performed using a Berkovich indenter (α=65°). As a Poisson's ratio, the Poisson's ratio of a cured body obtained by curing a curable composition was used. The test was performed under the conditions of a test load of 2.5 mN, a loading speed of 0.5 mN/sec, an unloading speed of 0.5 mN/sec, and a maximum load duration of 1 second, and an indentation elastic modulus was determined.

(2) Measurement Method for Micropore Volume
1.0 g of organic-inorganic composite particles were placed in a sample cell, and subjected to pretreatment by evacuation at 120° C. for 3 hours using a pretreatment apparatus ("Vacu-prep 061" manufactured by Shimadzu Corporation). After that, with the use of nitrogen as an adsorption gas and liquid nitrogen as a coolant, the micropore volume of pores having a micropore diameter in the range of from 1 nm to 500 nm was determined with a micropore distribution-measuring apparatus based on a gas adsorption method ("TriStar II 3020" manufactured by Shimadzu Corporation).

Production Example 1

100 Parts by mass of BMPEPP10 and 0.5 part by mass of BPO were uniformly mixed. 430 Parts by mass of the spray-dried aggregates of the inorganic particles D-1 were impregnated with 100 parts by mass of the mixture, and the resultant was heated at 100° C. for 1 hour to prepare organic-inorganic composite particles A(1). The organic-inorganic composite particles A(1) had an average particle diameter of 10 μm and a micropore volume of 0.10 cm$^3$/g.

Production Example 2

50 Parts by mass of BMPEPP10, 50 parts by mass of UDMA, and 0.5 part by mass of BPO were uniformly mixed. 430 Parts by mass of the spray-dried aggregates of the inorganic particles D-1 were impregnated with 100 parts by mass of the mixture, and the resultant was heated at 100° C. for 1 hour to prepare organic-inorganic composite particles A(2). The organic-inorganic composite particles A(2) had an average particle diameter of 10 μm and a micropore volume of 0.10 cm$^3$/g.

Production Example 3

50 Parts by mass of UDMA, 20 parts by mass of TEGDMA, 30 parts by mass of BMPEPP10, and 0.5 part by mass of BPO were uniformly mixed. 430 Parts by mass of the spray-dried aggregates of the inorganic particles D-1 were impregnated with 100 parts by mass of the mixture, and the resultant was heated at 100° C. for 1 hour to prepare organic-inorganic composite particles A(3). The organic-inorganic composite particles A(3) had an average particle diameter of 10 μm and a micropore volume of 0.10 cm$^3$/g.

Production Example 4

100 Parts by mass of BMPEPP2.6 and 0.5 part by mass of BPO were uniformly mixed. 430 Parts by mass of the spray-dried aggregates of the inorganic particles D-1 were impregnated with 100 parts by mass of the mixture, and the resultant was heated at 100° C. for 1 hour to prepare organic-inorganic composite particles A(4). The organic-inorganic composite particles A(4) had an average particle diameter of 10 μm and a micropore volume of 0.10 cm/g.

Production Example 5

100 Parts by mass of BMPEPP10 and 0.5 part by mass of BPO were uniformly mixed. 100 Parts by mass of the mixture and 300 parts by mass of the spray-dried aggregates of the inorganic particles D-1 were kneaded until the spray-dried aggregates of the inorganic particles D-1 were crushed and primary particles (individual inorganic particles D-1) were sufficiently dispersed in the mixture. The resultant was degassed, cured by heating at 100° C. for 1 hour, and pulverized using a ball mill to prepare organic-inorganic composite particles A(5). The organic-inorganic composite particles A(5) had an average particle diameter of 10 μm and a micropore volume of 0.00 cm$^3$/g.

Production Example 6

100 Parts by mass of BMPEPP10 and 0.5 part by mass of BPO were uniformly mixed. 340 Parts by mass of the spray-dried aggregates of the inorganic particles D-1 were impregnated with 100 parts by mass of the mixture, and the resultant was heated at 100° C. for 1 hour to prepare organic-inorganic composite particles A(6). The organic-inorganic composite particles A(6) had an average particle diameter of 10 μm and a micropore volume of 0.02 cm$^3$/g.

Production Example 7

100 Parts by mass of BMPEPP10 and 0.5 part by mass of BPO were uniformly mixed. 220 Parts by mass of the spray-dried aggregates of the inorganic particles D-1 were impregnated with 100 parts by mass of the mixture, and the resultant was heated at 100° C. for 1 hour to prepare organic-inorganic composite particles A(7). The organic-inorganic composite particles A(7) had an average particle diameter of 10 m and a micropore volume of 0.25 cm$^Y$/g.

Production Example 8

60 Parts by mass of Bis-GMA, 40 parts by mass of TEGDMA, and 0.5 part by mass of BPO were uniformly mixed. 430 Parts by mass of the spray-dried aggregates of the inorganic particles D-1 were impregnated with 100 parts by mass of the mixture, and the resultant was heated at 100° C. for 1 hour to prepare organic-inorganic composite particles A(8). The organic-inorganic composite particles A(8) had an average particle diameter of 10 μm and a micropore volume of 0.10 cm$^3$/g.

Production Example 9

60 Parts by mass of Bis-GMA, 40 parts by mass of TEGDMA, and 0.5 part by mass of BPO were uniformly mixed. 100 Parts by mass of the mixture and 300 parts by mass of the spray-dried aggregates of the inorganic particles D-1 were kneaded until the spray-dried aggregates of the inorganic particles D-1 were crushed and primary particles (individual inorganic particles D-1) were sufficiently dispersed in the mixture. The resultant was degassed, cured by heating at 100° C. for 1 hour, and pulverized using a ball mill to prepare organic-inorganic composite particles A(9). The organic-inorganic composite particles A(9) had an average particle diameter of 10 μm and a micropore volume of 0.00 cm$^3$/g.

Bending Test

A prepared curable composition was polymerized and cured to produce a cured body. Test pieces each measuring 2.0 mm wide by 2.0 mm thick by 25.0 mm long were cut out of the cured body, and polished with waterproof abrasive paper No. 1500. A three-point bending test was performed using a universal tester Autograph (manufactured by Shimadzu Corporation) in a room temperature atmosphere under the conditions of a support distance of 20 mm and a crosshead speed of 0.75 mm/min. Five test pieces were each measured for its bending strength [MPa] defined by the following equation and fracture energy [N/mm], and their average values were determined.

$$\text{Bending strength [MPa]} = 3FS/(2bh^2) \qquad \text{Equation}$$

In the equation, F represents the maximum load [N] applied to a test piece, S represents the support distance [mm], b represents the width [mm] of the test piece measured immediately before the test, and h represents the thickness [mm] of the test piece measured immediately before the test.

The fracture energy [N/mm] was determined by dividing the total energy [N·mm] applied until fracture of a test piece by the cross-sectional area [mm$^2$] of the test piece.

Example 1

75 Parts by mass of UDMA, 25 parts by mass of TEGDMA, and 0.5 part by mass of BPO were mixed to prepare a polymerizable monomer composition. To 20 parts by mass of the polymerizable monomer composition, 40 parts by mass of the organic-inorganic composite particles A(1) and 40 parts by mass of the spray-dried aggregates of the inorganic particles D-1 were added. While the forms of the organic-inorganic composite particles A(1) were kept, the mixture was kneaded until the spray-dried aggregates of the inorganic particles D-1 were crushed and primary particles (individual inorganic particles D-1) were sufficiently dispersed in a curable composition. The resultant was degassed to prepare a paste of a curable composition. The paste was subjected to pressure/heat polymerization at 100° C. for 1 hour to produce a cured body, which was subjected to the bending test.

Examples 2 to 5

Cured bodies were each produced by the same method as in Example 1 except for changing (A) the organic-inorganic composite particles and (B) polymerizable monomer used to a composition shown in Table 1, and were subjected to the bending test.

Example 6

75 Parts by mass of UDMA, 25 parts by mass of TEGDMA, 0.5 part by mass of CQ, and 0.5 part by mass of DMBE were mixed to prepare a polymerizable monomer composition. To 20 parts by mass of the polymerizable monomer composition, 40 parts by mass of the organic-inorganic composite particles A(5) and 40 parts by mass of the spray-dried aggregates of the inorganic particles D-1 were added. While the forms of the organic-inorganic composite particles A(5) were kept, the mixture was kneaded until the spray-dried aggregates of the inorganic particles D-1 were crushed and primary particles (individual inorganic particles D-1) were sufficiently dispersed in a curable composition. The resultant was degassed to prepare a paste of a curable composition. Both sides of the paste were irradiated with light for 2 minutes with a technical photoirradiation device Pearl Cure Light (manufactured by Tokuyama Dental Corporation) to produce a cured body, which was subjected to the bending test.

Examples 7 and 8

Cured bodies were each produced by the same method as in Example 1 except for changing (A) the organic-inorganic composite particles used to a composition shown in Table 1, and were subjected to the bending test.

Comparative Example 1

A cured body was produced by the same method as in Example 1 except for changing the organic-inorganic composite particles used to A(8), and was subjected to the bending test.

Comparative Example 2

A cured body was produced by the same method as in Example 6 except for changing the organic-inorganic composite particles used to A(9), and was subjected to the bending test.

Details of the curable compositions used in respective Examples and Comparative Examples, and the evaluation results of the bending strength and the fracture energy are shown in Table 1 and Table 2.

TABLE 1

| | (A) Organic-inorganic composite particles | | | | | | Matrix | | | |
|---|---|---|---|---|---|---|---|---|---|---|
| | | (a-1) Polymerizable monomer | | | | | (B) Polymerizable monomer | | | |
| | Kind | Kind and blending amount (parts by mass) | Molecular weight | Molecular weight per polymerizable functional group | Micropore volume [cm$^3$/g] | Elastic modulus P [GPa] | Kind and blending amount (parts by mass) | Molecular weight | Molecular weight per polymerizable functional group | Elastic modulus M [GPa] |
| Example 1 | A(1) | BMPEPP10 (100) | 804 | 402 | 0.10 | 1.9 | UDMA(75)/ TEGDMA (25) | 415 | 208 | 15.8 |
| Example 2 | A(2) | BMPEPP10 (50)/ UDMA (50) | 637 | 319 | 0.10 | 4.5 | UDMA(75)/ TEGDMA (25) | 415 | 208 | 15.8 |
| Example 3 | A(1) | BMPEPP10 (100) | 804 | 402 | 0.10 | 1.9 | TMPT(50)/ UDMA(37.5)/ TEGDMA(12.5) | 382 | 163 | 18.8 |
| Example 4 | A(3) | UDMA (50)/ TEGDMA (20)/ BMPEPP10(30) | 533 | 267 | 0.10 | 7.8 | UDMA(75)/ TEGDMA (25) | 415 | 208 | 15.8 |
| Example 5 | A(4) | BMPEPP2.6 (100) | 478 | 239 | 0.10 | 11.2 | UDMA(75)/ TEGDMA (25) | 415 | 208 | 15.8 |
| Example 6 | A(5) | BMPEPP10 (100) | 804 | 402 | 0.00 | 1.9 | UDMA(75)/ TEGDMA (25) | 415 | 208 | 15.8 |
| Example 7 | A(6) | BMPEPP10 (100) | 804 | 402 | 0.02 | 1.8 | UDMA(75)/ TEGDMA (25) | 415 | 208 | 15.8 |
| Example 8 | A(7) | BMPEPP10 (100) | 804 | 402 | 0.25 | 2.0 | UDMA(75)/ TEGDMA (25) | 415 | 208 | 15.8 |

TABLE 1-continued

| | | (A) Organic-inorganic composite particles | | | | | Matrix | | | |
| | | (a-1) Polymerizable monomer | | | | | (B) Polymerizable monomer | | | |
| | Kind | Kind and blending amount (parts by mass) | Molecular weight | Molecular weight per polymerizable functional group | Micropore volume [cm³/g] | Elastic modulus P [GPa] | Kind and blending amount (parts by mass) | Molecular weight | Molecular weight per polymerizable functional group | Elastic modulus M [GPa] |
| --- | --- | --- | --- | --- | --- | --- | --- | --- | --- | --- |
| Comparative Example 1 | A(8) | BisGMA(60)/ TEGDMA (40) | 422 | 211 | 0.10 | 13.4 | UDMA(75)/ TEGDMA (25) | 415 | 208 | 15.8 |
| Comparative Example 2 | A(9) | BisGMA(60)/ TEGDMA(40) | 422 | 211 | 0.00 | 13.4 | UDMA(75)/ TEGDMA (25) | 415 | 208 | 15.8 |

TABLE 2

| | Elastic modulus M- elastic modulus P [GPa] | Bending strength [MPa] | Fracture energy [N/mm] |
| --- | --- | --- | --- |
| Example 1 | 13.9 | 219 | 8.7 |
| Example 2 | 11.3 | 216 | 7.5 |
| Example 3 | 16.9 | 215 | 7.6 |
| Example 4 | 8.0 | 210 | 6.9 |
| Example 5 | 4.6 | 208 | 5.6 |
| Example 6 | 13.9 | 158 | 6.5 |
| Example 7 | 14.0 | 195 | 6.5 |
| Example 8 | 13.8 | 215 | 6.8 |
| Comparative Example 1 | 2.4 | 201 | 4.4 |
| Comparative Example 2 | 2.4 | 144 | 3.2 |

The invention claimed is:

1. A curable composition, comprising:
organic-inorganic composite particles, each of the organic-inorganic composite particles including an organic resin and inorganic particles;
a first polymerizable monomer;
a polymerization initiator; and
inorganic particles,
wherein a cured body formed by curing the curable composition includes:
   a matrix formed by curing all constituent components of the curable composition except for the organic-inorganic composite particles; and
   the organic-inorganic composite particles dispersed and contained in the cured body,
wherein an elastic modulus M of the matrix is larger than an elastic modulus P of the organic-inorganic composite particles by 3.0 GPa or more,
wherein the organic resin comprises a cured body of a second polymerizable monomer having a molecular weight per polymerizable functional group contained in a molecule that is in the range of 230 to 1000, and
wherein a molecular weight per polymerizable functional group contained in the first polymerizable monomer is in the range of 100 to 210.

2. A curable composition according to claim 1,
wherein the elastic modulus P of the organic-inorganic composite particles is from 0.01 GPa to 12.0 GPa, and
wherein the elastic modulus M of the matrix is from 6.0 GPa to 30.0 GPa.

3. A curable composition according to claim 1,
wherein the organic-inorganic composite particles have micropores, and
wherein the organic-inorganic composite particles that have micropores have a micropore volume of from 0.01 cm³/g to 0.30 cm³/g.

4. A curable composition according to claim 1,
wherein an elastic modulus difference A of the elastic modulus M minus the elastic modulus P is from 5 GPa to 18 GPa, and
wherein the second polymerizable monomer has a molecular weight per polymerizable functional group contained in a molecule that is in the range of 230 to 1000.

* * * * *